(12) United States Patent
Asa

(10) Patent No.: US 6,170,359 B1
(45) Date of Patent: Jan. 9, 2001

(54) MICRO TUBE CAP OPENING DEVICE WITH TUBE HOLDER AND SLIDABLE LIFTING BAR

(75) Inventor: David Asa, Carmel, CA (US)

(73) Assignee: Michael Hoffman, Carmel, CA (US)

( * ) Notice: Under 35 U.S.C. 154(b), the term of this patent shall be extended for 0 days.

(21) Appl. No.: 09/396,297

(22) Filed: Sep. 15, 1999

Related U.S. Application Data

(60) Provisional application No. 60/100,587, filed on Sep. 16, 1998.

(51) Int. Cl.⁷ .................................................. B67B 7/00
(52) U.S. Cl. .............................. 81/3.39; 81/3.36; 220/740
(58) Field of Search ................................... 81/3.36, 3.39, 81/3.55; 220/740

(56) References Cited

U.S. PATENT DOCUMENTS

| 4,683,782 | 8/1987 | Warburg | 81/3.57 |
| 4,858,502 | 8/1989 | Warburg | 81/3.57 |
| 5,253,551 | * 10/1993 | DeVaughn | 81/3.09 |
| 5,348,181 | * 9/1994 | Smith et al. | 220/254 |
| 5,392,943 | * 2/1995 | Delatte et al. | 220/475 |

FOREIGN PATENT DOCUMENTS 879 062 * 6/1953 (GB) .................................. 81/3.36

* cited by examiner

Primary Examiner—Stephen F. Gerrity
Assistant Examiner—Hadi Shakeri
(74) Attorney, Agent, or Firm—Flanagan & Flanagan; John K. Flanagan; John R. Flanagan

(57) ABSTRACT

A micro tube cap opening device includes a tubular holder, a lifting bar and a mounting sleeve. The holder has a well supported by a sidewall of the holder and open at a first end thereof for receiving therein a tube body of a micro tube. The mounting sleeve is attached on and along the sidewall of the holder. The lifting bar is slidably mounted by and through the mounting sleeve to undergo movement between a retracted position and an extended position. A first end of the lifting bar in the retracted position is disposed adjacent to the first end of the holder and adjacent to a cap of the micro tube in a closed position interference fitted into the tube body of the micro tube when the tube body of the micro tube is disposed within the well of the holder. The first end of the lifting bar in the extended position is disposed outwardly from the first end of the holder such that the cap of the micro tube is forced into an open position in response to engagement of the lifting bar therewith upon movement of the lifting bar from the retracted to extended position.

20 Claims, 2 Drawing Sheets

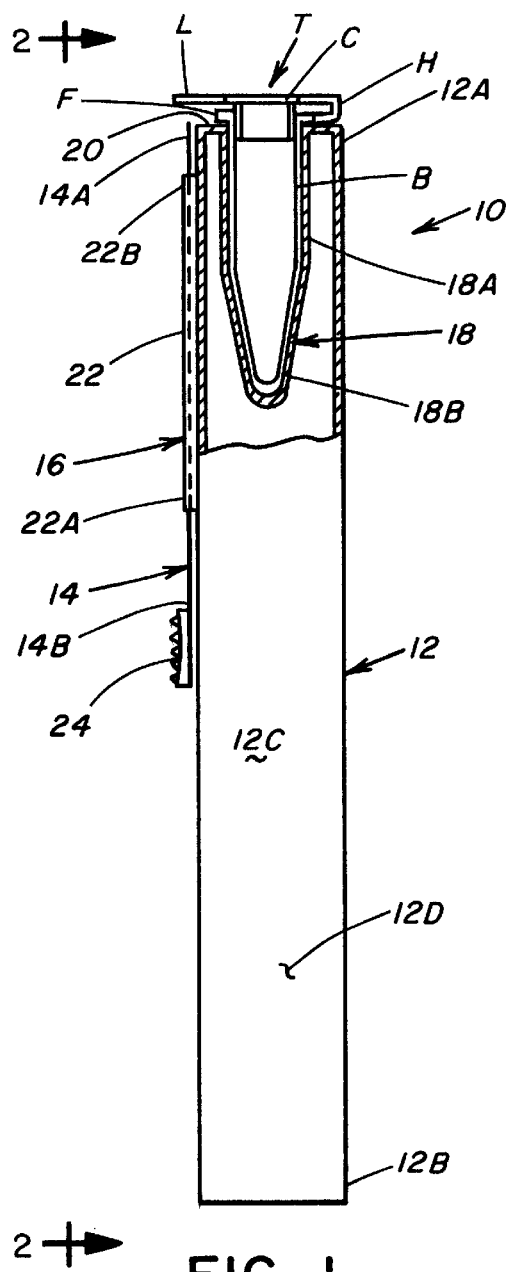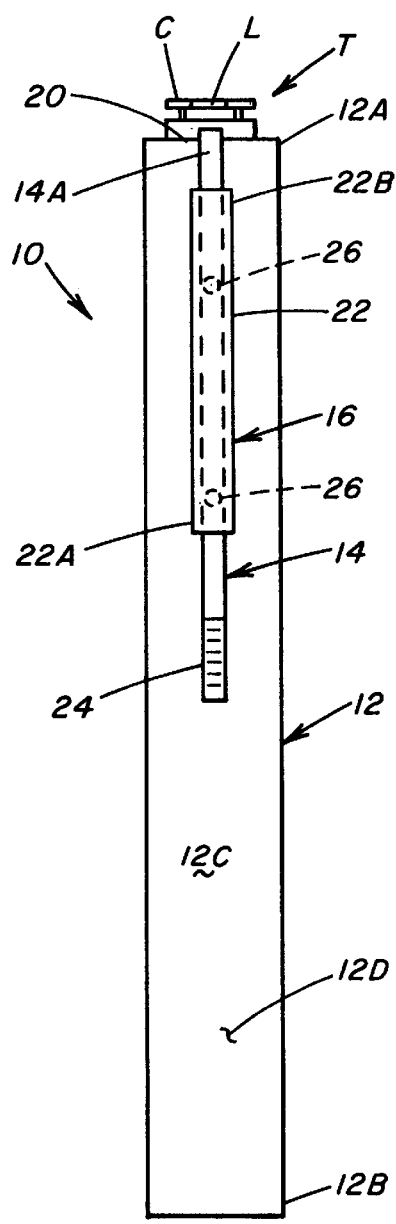
FIG. 1
FIG. 2

MICRO TUBE CAP OPENING DEVICE WITH TUBE HOLDER AND SLIDABLE LIFTING BAR

This patent application claims the benefit of U.S. provisional application No. 60/100,587, filed Sep. 16, 1998.

BACKGROUND OF THE INVENTION

1. Field of the Invention

The present invention generally relates to means for opening microcentrifuge and test tubes (hereinafter referred to as "micro" tubes) and, more particularly, is concerned with a micro tube cap opening device having a tube holder for receiving and holding the tube and a slidable lifting bar on the tube holder for lifting the cap off the tube.

2. Description of the Prior Art

Micro tubes are small plastic tubes having a tube body capable of holding only a small amount of a liquid. Such tubes typically have a lid or cap which is attached to the tube body by a hinge strip and fits into an open upper end of the tube body by an interference fit. The interference fit of the cap with the upper end of the tube body tends to be quite snug in order to be liquid tight. The snug fit of the cap in the tube body upper end makes the cap difficult to remove therefrom and thus open in order to gain access to the contents inside the tube body.

A significant degree of risk of splashing or spilling the contents of a tube exists due to the force required to overcome the level of resistance created by the high coefficient of friction between the cap and the upper end of the tube body. This can be especially hazardous if the contents of the tube is toxic or infectious or has as part of the contents a radioactive isotope, such as one used as a marker for identification purposes. If the contents splashes or spills out of the tube, a person holding the tube is at risk of coming in contact with these substances.

Further, whenever radioactive materials are spilled, a substantial amount of paper work and reporting of the incident is required, irrespective of the level of radiation or of where the accident occurred. The health risk and extra work associated with spills are undesirable.

Also, some of the smallest tubes have volumes of two milliliters or less and are approximately one half inch in diameter and one half inch in length. The small size of these tubes makes them particularly difficult to handle. Manually opening the smallest tubes can be a fatiguing process, especially if the person must repeat the process many times over, as is often the case. Typically, the person employs both hands, one hand to hold the tube body and the other hand to open the cap of the tube. Yet, the person should have one hand available for pipetting liquids into and from the tube, while holding and opening or closing the tube. Efficient operation of a pipette is generally not achievable if the person must use both hands to manipulate the tube.

Devices have been developed for use in opening the caps of micro tubes. A representative example of a device is the one disclosed in U.S. Pat. Nos. 4,683,782 and 4,858,502 to Warburg. The Warburg device is a hand-held opener having a handle and a base at one end of the handle with a recess shaped to accept a lip projection of the cap on the tube. The Warburg opener may be actuated by a free hand of the person to remove the cap from the tube body. However, the Warburg opener requires that the tube body be disposed in a well of a separate tube rack or held by the other hand of the user. Thus, while the Warburg opener may be satisfactory in use under the specific conditions for which it was designed to function, it does not seem to provide an optimum solution for the problems at hand.

Consequently, a need still exists for an innovation which provides a more effective solution to the aforementioned problems in the prior art and without introducing any new problems in place thereof.

SUMMARY OF THE INVENTION

The present invention provides a micro tube cap opening device which is designed to satisfy the aforementioned need. The micro tube cap opening device of the present invention is ergometrically designed to allow a person to securely hold a micro tube in one hand and with the same hand open a cap of the micro tube in a safe and secure manner while pipetting with the other hand. The micro tube cap opening device also prevents or greatly reduces the possibility of the contents of the micro tube from splashing or spilling out in the process of opening the cap of the micro tube.

Accordingly, the present invention is directed to a micro tube cap opening device which comprises: (a) an elongated tubular holder having opposite first and second ends, a continuous sidewall with an exterior surface extending between the first and second ends and a well supported by the sidewall within and open at the first end of the holder for receiving therein a tube body of a micro tube, the sidewall of the holder providing a handle enabling a person with the same hand to grip the holder with the micro tube received in the well and to operate the device; (b) a lifting bar having opposite first and second ends; and (c) means provided on and along the exterior surface of the sidewall of the holder for slidably mounting the lifting bar on the sidewall to undergo movement between a retracted position and an extended position, the first end of the lifting bar in the retracted position being disposed adjacent to the first end of the holder and adjacent to a cap of the micro tube in a closed position interference fitted into the tube body of the micro tube when the tube body of the micro tube is disposed within the well of the holder, the first end of the lifting bar in the extended position being disposed outwardly from the first end of the holder such that the cap of the micro tube is forced into an open position in response to engagement of the lifting bar therewith upon movement of the lifting bar from the retracted position to the extended position.

More particularly, the tubular holder has a substantially cylindrical configuration. The well of the holder has a size and a configuration substantially conforming, respectively, to a size and a configuration of the tube body of the micro tube. The first end of the holder has an annular endwall disposed in a substantially transverse relationship to the sidewall of the holder and surrounding the well at the first end of the holder for receiving thereon in a substantially abutting juxtaposed relationship a flange formed on the tube body of the micro tube adjacent to an end of the tube body of the micro tube where the cap of the micro tube is located.

Further, the lifting bar has an actuation portion at the second end thereof for receiving a thumb of the person for pushing the lifting bar into the extended position from the retracted position and for pulling the lifting bar into the retracted position from the extended position. The actuation portion of the lifting bar has a substantially concave configuration substantially conforming to the shape of the thumb of the person gripping the holder. The actuation portion of the lifting bar can have a substantially textured gripping surface.

The means for slidably mounting the lifting bar is a mounting sleeve having opposite open first and second ends and being attached to the exterior surface of the sidewall of the holder. The lifting bar is slidably mounted to and disposed through the mounting sleeve such that the first and second ends of the lifting bar are disposed exteriorly of the mounting sleeve in each of the retracted and extended positions. The lifting bar has at least one stop element formed thereon which engages the mounting sleeve and frictionally retains the lifting bar in place within the mounting sleeve when the lifting bar is stationary and which deforms upon the lifting bar undergoing sliding movement so as to allow the lifting bar to move between the retracted and extended positions.

These and other features and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the following detailed description, reference will be made to the attached drawings in which:

FIG. 1 is a side elevational view, with portions in longitudinal sectional form, of a micro tube cap opening device of the present invention showing a tube body of a micro tube disposed within a well of a holder of the device, a slidable lifting bar of the device in a retracted position and a cap of the micro tube in a closed position.

FIG. 2 is a front elevational view of the device as seen along line 2—2 of FIG. 1.

DETAILED DESCRIPTION OF THE INVENTION

Figure 3:
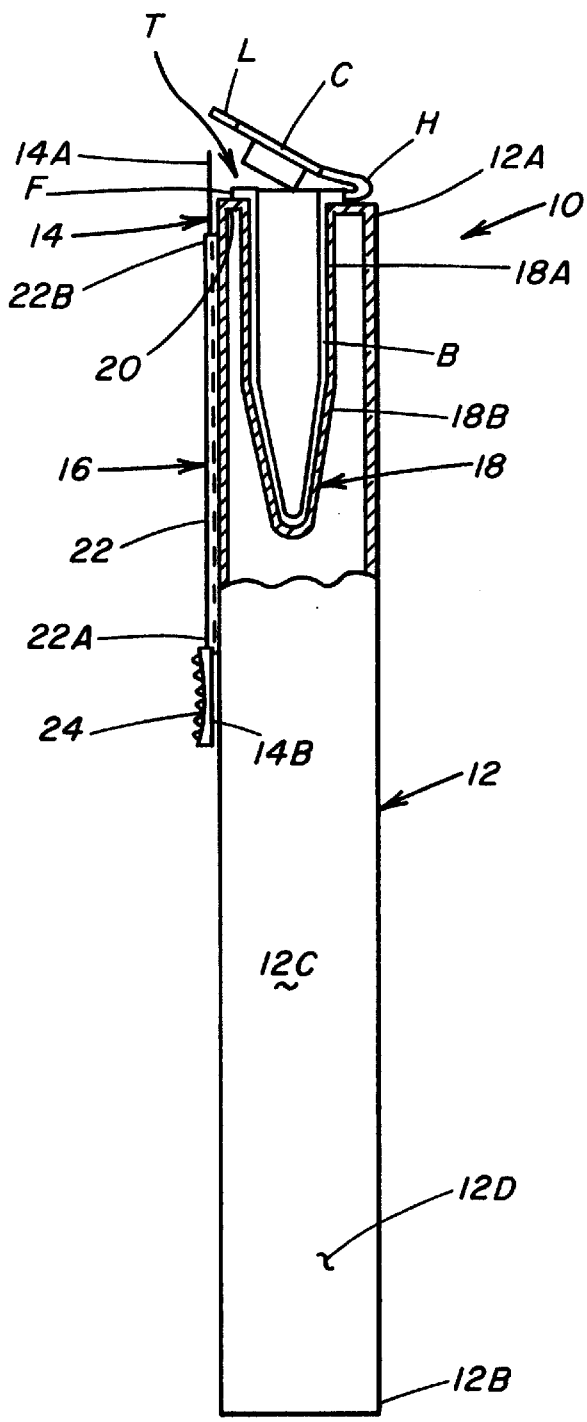
FIG. 3 is another view of the device similar to that FIG. 1 but showing the slidable lifting bar in an extended position and the cap of the micro tube in an open position after having been forced into the open position upon engagement by and movement of the slidable lifting bar from the retracted position to the extended position.

Referring to the drawings and particularly to FIGS. 1 to 3, there is illustrated a micro tube cap opening device, generally designated 10, of the present invention. The micro tube cap opening device 10 is adapted for use with a micro tube T having a cap C and a tube body B. The cap C is fitted into the tube body B by interference fit. The cap C is snug in order to be liquid tight. The cap C is attached to the tube body B by a hinge strap H, such as a living hinge. The cap C has a lip L formed thereon opposite from the hinge H. The micro tube cap opening device 10 basically includes an elongated tubular holder 12, a lifting bar 14 and means 16 for slidably mounting the lifting bar 14 on the tubular holder 12.

The tubular holder 12 of the device 10 has a generally cylindrical configuration, though need not be so limited. The holder 12 has opposite first and second ends 12A, 12B and a continuous sidewall 12C with an exterior surface 12D extending between the first and second ends 12A, 12B. The holder 12 has a length extending between the first and second ends 12A, 12B thereof which is substantially greater than a diameter of the holder 12. The holder 12 also has a tubular well 18 open at the first end 12A of the holder 12 for receiving therein the tube body B of the micro tube T. The well 18 has a size and configuration conforming, respectively, to the size and configuration of the tube body B of the micro tube T. By way of example, the well 18 has an upper portion 18A and a lower portion 18B. The upper portion 18A of the well 18 comprises about half to two-thirds of the length of the well 18. The lower portion 18B of the well 18 comprises about one-third to half of the well 18. The upper portion 18A has a substantially cylindrical configuration. The lower portion 18B has a substantially conical or tapered configuration. The tube body B of the typical micro tube T is similarly configured such that the internal design of the well 18 keeps the tube body B in position for pipetting without any significant play within the well 18. The sidewall 12C of the holder 12 provides a handle enabling a person with the same hand to hold the holder 12 with the micro tube received in the well and to operate the device 10.

The first end 12A of the holder 12 has an annular endwall 20 disposed in substantially transverse relation to the side wall 12C of the holder 12. The annular endwall 20 surrounds the well 18 at the first end 12A of the holder 12 and receives thereon in a substantially abutting juxtaposed relationship a flange F formed on the tube body B of the micro tube T. The flange F is disposed adjacent to an end of the tube body B of the micro tube T where the cap C of the micro tube T is located. The annular endwall 20 also helps keep the tube body B in position.

The means 16 for slidably mounting the lifting bar 14 is a mounting sleeve 22. The mounting sleeve 22 has a generally rectangular transverse configuration, though need not be so limited, which substantially conforms to the configuration of the lifting bar 14. The mounting sleeve 22 has a transverse area which is slightly greater than a transverse area of the lifting bar 14. The mounting sleeve 22 has opposite open first and second ends 22A, 22B and is attached to the sidewall 12C of the handle 12. The mounting sleeve 22 has a length extending between the first and second ends 22A, 22B thereof which is less than the length of the lifting bar 14. The lifting bar 14 is slidably mounted to and disposed through the mounting sleeve 22 such that first and second ends 14A, 14B of the lifting bar 14 are disposed exteriorly of the mounting sleeve 22 in each of the retracted and extended positions.

The lifting bar 14 of the device 10 has a substantially rectangular transverse configuration, though need not be so limited. The lifting bar 14 has a length extending between the first and second ends 14A, 14B thereof which is less than the length of the holder 12. The lifting bar 14 is slidably mounted to the side wall 12C of the holder 12 to undergo reciprocal movement between a retracted position, as shown in FIG. 1, and an extended position, as shown in FIG. 3. The first end 14A of the lifting bar 14 in the retracted position, as shown in FIG. 1, is disposed adjacent to the first end 12A of the holder 12 and spaced from but adjacent to the cap C of the micro tube T in a closed position interference fitted into the tube body B of the micro tube T when the tube body B of the micro tube T is disposed within the well 16 of the holder 12. The first end 14A of the lifting bar 14 in the extended position, as shown in FIG. 3, is disposed outwardly from the first end 12A of the holder 12 such that the cap C of the micro tube T is forced into an open position in response to engagement of the lifting bar 14 therewith upon movement of the lifting bar 14 from the retracted position to the extended position.

The cap C of the micro tube T is forced into the open position by the first end 14A of the lifting bar 14 pressing upwardly against the lip L of the cap C. The upward movement of the lifting bar 14 applies a controlled force which separates the cap C from the tube body B of the micro tube T in a manner which prevents or greatly reduces the possibility of the contents of the micro tube T from splashing or spilling out in the process.

The lifting bar 14 has an actuation portion 24 at the second end 14B thereof for receiving a thumb (not shown) of a user for pushing the lifting bar 14 into the extended position from the retracted position and for pulling the lifting bar 14 into the retracted position from the extended position. The actuation portion 24 of the lifting bar 14 has a substantially concave configuration substantially conforming to a shape of the thumb of the user gripping the holder 12. The actuation portion 24 also has a substantially textured gripping surface which, along with the substantially concave configuration, ensures that the thumb of the user does not slip while moving the lifting bar 14 upward and downward. The holder 12 and the lifting bar 14 together allow the user to securely grip the holder 12 with the micro tube T in one hand and with the same hand open the cap C of the micro tube T in a safe and secure manner while pipetting with the other hand.

The lifting bar 14 has at least one and, preferably, a plurality of stop elements 26 in the form of dimples formed on the lifting bar 14. The stop elements 26 engage the mounting sleeve 22 and frictionally retain the lifting bar 14 in place within the mounting sleeve 22 when the lifting bar 14 is stationary, such as when the lifting bar 14 is disposed in one of the retracted and extended positions. The stop elements 26 deform by compressing upon sliding movement of the lifting bar 14 to allow the lifting bar 14 to move between the retracted and extended positions. The stop elements 26, alternatively, may be formed on and disposed within the mounting sleeve 22.

Each of the holder 12, the lifting bar 14 and the mounting sleeve 22 are preferably, but not necessarily, made from a moldable plastic material, such as a plastic resin. The holder 12 and the mounting sleeve 22 are molded as one part. The lifting bar 14 is molded as a separate part from the holder 12 and the mounting sleeve 22. The parts are fabricated by using any suitable conventional technique, such as injection molding of the plastic resin. The parts are assembled together in a secondary, post molding process.

It is thought that the present invention and its advantages will be understood from the foregoing description and it will be apparent that various changes may be made thereto without departing from the spirit and scope of the invention or sacrificing all of its material advantages, the form hereinbefore described being merely preferred or exemplary embodiment thereof.

I claim:

1. A micro tube cap opening device, comprising:
   (a) an elongated tubular holder having opposite first and second ends, a continuous sidewall with an exterior surface extending between said first and second ends and a well supported by said sidewall within and open at said first end of said holder for receiving therein a tube body of a micro tube, said sidewall of said holder providing a handle enabling a person with the same hand to grip said holder with the micro tube received in said well and to operate said device;
   (b) a lifting bar having opposite first and second ends; and
   (c) means provided on and along said exterior surface of said sidewall of said holder for slidably mounting said lifting bar on said sidewall to undergo movement between a retracted position and an extended position, said first end of said lifting bar in said retracted position being disposed adjacent to said first end of said holder and adjacent to a cap of the micro tube in a closed position interference fitted into the tube body of the micro tube when the tube body of the micro tube is disposed within said well of said holder, said first end of said lifting bar in said extended position being disposed outwardly from said first end of said holder such that the cap of the micro tube is forced into an open position in response to engagement of said lifting bar therewith upon movement of said lifting bar from said retracted position to said extended position.

2. The device of claim 1 wherein said tubular holder has a substantially cylindrical configuration.

3. The device of claim 1 wherein said well of said tubular holder has a size and a configuration substantially conforming, respectively, to a size and a configuration of the tube body of the micro tube.

4. The device of claim 1 wherein said first end of said tubular holder has an annular endwall disposed in a generally transverse relationship to said sidewall of said holder and surrounding said well at said first end of said holder for receiving thereon in a substantially abutting juxtaposed relationship a flange formed on the tube body of the micro tube adjacent to an end of the tube body of the micro tube where the cap of the micro tube is located.

5. The device of claim 1 wherein said lifting bar has an actuation portion at said second end thereof for receiving a thumb of a person for pushing said lifting bar into said extended position from said retracted position and for pulling said lifting bar into said retracted position from said extended position.

6. The device of claim 5 wherein said actuation portion of said lifting bar has a substantially concave configuration substantially conforming to a shape of the thumb of the person gripping said holder.

7. The device of claim 5 wherein said actuation portion of said lifting bar has a substantially textured gripping surface.

8. The device of claim 1 wherein:
   said means for slidably mounting said lifting bar is a mounting sleeve having opposite open first and second ends and being attached to said exterior surface of said sidewall of said holder; and
   said lifting bar is slidably mounted to and disposed through said mounting sleeve such that said first and second ends of said lifting bar are disposed exteriorly of said mounting sleeve in each of said retracted and extended positions.

9. The device of claim 8 wherein said lifting bar has at least one stop element formed thereon which engages said mounting sleeve and frictionally retains said lifting bar in place within said mounting sleeve when said lifting bar is stationary and which deforms upon said lifting bar undergoing sliding movement so as to allow said lifting bar to move between said retracted and extended positions.

10. A micro tube cap opening device, comprising:
   (a) an elongated tubular holder having opposite first and second ends, a continuous sidewall with an exterior surface extending between said first and second ends and a well supported by said sidewall within an upper portion of said sidewall and open at said first end of said holder and having a cylindrical upper portion and a conical lower portion so as to provide a configuration substantially conforming to and for receiving therein a tube body of a micro tube, said sidewall of said holder providing a handle enabling a person with the same hand to grip said holder with the micro tube received in said well and to operate said device;
   (b) a lifting bar having opposite first and second ends and an actuation portion at said second end of said lifting bar; and (c) means provided on and along said exterior surface of said sidewall of said holder for slidably mounting said lifting bar on said sidewall to undergo movement between a retracted position and an extended position, said first end of said lifting bar in said retracted position being disposed adjacent to said first end of said holder and adjacent to a cap of the micro tube in a closed position interference fitted into the tube body of the micro tube when the tube body of the micro tube is disposed within said well of said holder, said first end of said lifting bar in said extended position being disposed outwardly from said first end of said holder such that the cap of the micro tube is forced into an open position in response to engagement of said lifting bar therewith upon movement of said lifting bar from said retracted position to said extended position, said actuation portion of said lifting bar for receiving a thumb of the person gripping said holder for pushing said lifting bar into said extended position from said retracted position and for pulling said lifting bar into said retracted position from said extended position.

11. The device of claim 10 wherein said first end of said tubular holder has an annular endwall disposed in a generally transverse relationship to said sidewall of said holder and surrounding said well at said first end of said holder for receiving thereon in a substantially abutting juxtaposed relationship a flange formed on the tube body of the micro tube adjacent to an end of the tube body of the micro tube where the cap of the micro tube is located.

12. The device of claim 10 wherein said actuation portion of said lifting bar has a substantially concave configuration substantially conforming to a shape of the thumb of the person gripping said holder.

13. The device of claim 10 wherein said actuation portion of said lifting bar has a substantially textured gripping surface.

14. The device of claim 10 wherein:
said means for slidably mounting said lifting bar is a mounting sleeve having opposite open first and second ends and being attached to said exterior surface of said sidewall of said holder; and
said lifting bar is slidably mounted to and disposed through said mounting sleeve such that said first and second ends of said lifting bar are disposed exteriorly of said mounting sleeve in each of said retracted and extended positions.

15. The device of claim 14 wherein said lifting bar has at least one stop element formed thereon which engages said mounting sleeve and frictionally retains said lifting bar in place within said mounting sleeve when said lifting bar is stationary and which deforms upon said lifting bar undergoing sliding movement so as to allow said lifting bar to move between said retracted and extended positions.

16. A microcentrifuge tube opening device, comprising:
(a) an elongated tubular holder having opposite first and second ends, a continuous sidewall with an exterior surface extending between said first and second ends and a well supported by said sidewall within an upper portion of said sidewall and open at said first end of said holder, said sidewall of said holder providing a handle enabling a person with the same hand to grip said holder with the micro tube received in said well and to operate said device;
(b) a mounting sleeve having opposite open first and second ends and being attached to and along said sidewall of said holder; and
(c) a lifting bar having opposite first and second ends and an actuation portion at said second end thereof, said lifting bar slidably mounted to and disposed through said mounting sleeve to undergo movement between a retracted position and an extended position, said first end of said lifting bar in said retracted position being disposed adjacent to said first end of said handle and adjacent to a cap of the micro tube in a closed position interference fitted into the tube body of the micro tube when the tube body of the micro tube is disposed within said well of said holder, said first end of said lifting bar in said extended position being disposed outwardly from said first end of said holder such that the cap of the micro tube is forced into an open position in response to engagement of said lifting bar therewith upon movement of said lifting bar from said retracted position to said extended position, said actuation portion of said lifting bar for receiving a thumb of the person gripping said holder for pushing said lifting bar into said extended position from said retracted position and for pulling said lifting bar into said retracted position from said extended position, said first and second ends of said lifting bar being disposed exteriorly of said mounting sleeve in each of said retracted and extended positions.

17. The device of claim 16 wherein said first end of said tubular holder has an annular endwall disposed in a generally transverse relationship to said sidewall of said holder and surrounding said well at said first end of said holder for receiving thereon in a substantially abutting juxtaposed relationship a flange formed on the tube body of the micro tube adjacent to an end of the tube body of the micro tube where the cap of the micro tube is located.

18. The device of claim 16 wherein said actuation portion of said lifting bar has a substantially concave configuration substantially conforming to a shape of the thumb of the person gripping said holder.

19. The device of claim 16 wherein said actuation portion of said lifting bar has a substantially textured gripping surface.

20. The device of claim 16 wherein said lifting bar has at least one stop element formed thereon which engages said mounting sleeve and frictionally retains said lifting bar in place within said mounting sleeve when said lifting bar is stationary and which deforms upon said lifting bar undergoing sliding movement so as to allow said lifting bar to move between said retracted and extended positions.

* * * * *